US006217531B1

(12) United States Patent
Reitmajer

(10) Patent No.: US 6,217,531 B1
(45) Date of Patent: Apr. 17, 2001

(54) ADJUSTABLE ELECTRODE AND RELATED METHOD

(75) Inventor: Ralph Reitmajer, Reichenbach an der Fils (DE)

(73) Assignee: ITS Medical Technologies & Services GmbH, Constance (DE)

( * ) Notice: Subject to any disclaimer, the term of this patent is extended or adjusted under 35 U.S.C. 154(b) by 0 days.

(21) Appl. No.: 09/178,625

(22) Filed: Oct. 26, 1998

(30) Foreign Application Priority Data

Oct. 24, 1997 (DE) ..................................... 8754829

(51) Int. Cl.[7] ..................................... A61B 17/22
(52) U.S. Cl. ..................................... 601/4; 367/147
(58) Field of Search ..................................... 601/2–4; 600/439; 367/146, 147

(56) References Cited

U.S. PATENT DOCUMENTS

| | | |
|---|---|---|
| 4,608,983 | 9/1986 | Müller et al. . |
| 4,685,461 | 8/1987 | Forssmann et al. . |
| 4,730,614 | 3/1988 | Lacruche et al. . |
| 4,809,682 | 3/1989 | Forssmann et al. . |
| 4,868,791 * | 9/1989 | Cathignol et al. . |
| 4,905,673 | 3/1990 | Pimiskern . |
| 4,928,671 * | 5/1990 | Reichenberger et al. . |
| 4,934,353 | 6/1990 | Nowacki et al. . |
| 4,938,781 | 7/1990 | Pimiskern . |
| 5,047,685 | 9/1991 | Nowacki et al. . |
| 5,109,338 * | 4/1992 | Ermert et al. . |
| 5,146,912 | 9/1992 | Eizenhoefer . |
| 5,195,508 | 3/1993 | Müller et al. . |
| 5,245,988 | 9/1993 | Einars et al. . |
| 5,420,473 | 5/1995 | Thomas . |
| 5,458,652 | 10/1995 | Uebelacker . |

FOREIGN PATENT DOCUMENTS

| | | |
|---|---|---|
| 26 35 635 | 2/1978 | (DE) . |
| 35 43 881 C1 | 12/1985 | (DE) . |
| 3804993 C1 | 2/1988 | (DE) . |
| 0 288 751 | 3/1989 | (EP) . |
| 0 419 791 A1 | 7/1990 | (EP) . |
| 0 457 037 A1 | 4/1991 | (EP) . |
| 0 590 177 A1 | 9/1992 | (EP) . |

* cited by examiner

*Primary Examiner*—Marvin M. Lateef
*Assistant Examiner*—Shawna J. Shaw
(74) *Attorney, Agent, or Firm*—McDermott, Will & Emery

(57) ABSTRACT

The present invention relates to a electrode assembly and related method that includes a insulator assembly, an electrode assembly, a charging system, a mechanism for measuring electrical voltages, a mechanism for adjusting the distance between inner and outer electrode tips, and a controller. The insulator assembly includes an insulator body having a hollow central portion with a threaded inner wall. The insulator assembly includes inner and outer conductors that are electrically connected to the charging system and are physically connected to inner and outer electrodes, respectively. The electrodes are positioned such that their longitudinal axes are aligned and the tips of the electrodes are in relatively close physical proximity. The distance between the tips is defined as the spark gap. The charging system charges a capacitor that discharges and forms a spark across the spark gap. The electrical measuring mechanism measures the discharge voltage of the capacitor and the controller compares it to a reference voltage, issuing a correction signal to the adjusting mechanism that repositions the electrodes, thus optimizing the spark gap. An alternate embodiment analyzes the charge and discharge characteristics of an electrode assembly that utilizes a second capacitor and an inductor to adjust the spark gap.

25 Claims, 6 Drawing Sheets

ADJUSTABLE ELECTRODE AND RELATED METHOD

BACKGROUND OF THE INVENTION

The present application claims foreign priority based on German application 197 46 972 filed on Oct. 24, 1997.

1. Field of the Invention

The present invention relates to the area of lithotripters; more particularly, a lithotripter electrode having an automatically adjusting spark gap.

2. Description of Related Art

Lithotripters exist for the contact-free destruction of concrements, e.g. kidney stones, in living bodies. Such devices are also used for the treatment of orthopedic ailments such as heal spurs and tennis elbow as well as non-union of bone problems. Lithotripters and related hardware are described in a number of patents; all of those mentioned below are hereby incorporated by reference.

Lithotripters use an electric underwater spark to generate the shock waves necessary to effect treatment. The spark is generated by an electrode usually mounted in a reflector that is used to focus the shock waves. Examples of these attempts may be found disclosed in U.S. Pat. Nos. 4,608,983 and 4,730,614.

In general, shock wave generation uses a spark produced by a discharge between electrodes. The discharge across the spark gap results from the discharge of an electrical capacitor. Varying the amount of the charging voltage of the capacitor regulates the shock wave energy. A larger or smaller voltage results in the formation of a stronger or weaker spark and thus modifies the strength of the shock wave and the size of the therapeutically active focus and thus in turn the applied shock wave energy.

It is desirable to provide a broad energy spectrum because of the various energy levels of shock waves used to treat different ailments. However, the voltage cannot be varied at will without replacing the electrode assembly because the spark gap, the gap between the electrodes, controls the discharge process. A wider gap requires a larger minimum voltage to bridge the distance between the two electrodes with a spark.

Early lithotripter electrodes used a fixed spark gap. One disadvantage to a fixed-gap electrode is that the electrodes slowly burn away after repeated use, thus increasing the spark gap distance and requiring a greater amount of voltage to generate a spark. But the larger gap and larger minimum voltage produces a stronger shock wave. One invention intended to resolve the electrode burn off issue is disclosed in U.S. Pat. No. 4,809,682.

Another disadvantage is that a low energy shock wave requires a low amount of voltage to be used with a relatively narrow spark gap while a high-energy shock wave requires a large amount of voltage to be used with a relatively wide spark gap. Accordingly, low energy shock waves could not be generated immediately following treatment using high-energy shock waves and vice versa without wholesale replacement of the electrode assembly. If an electrode assembly with a relatively small spark gap is used with a higher voltage, an energy-inefficient spark is produced because a portion of the energy bleeds off into the surroundings and is transformed into acoustic energy while another portion is transformed into heat energy and does not contribute to the formation of the shock wave. In other words, the proper voltage applied to the capacitor must be matched with a proper spark gap to produce an efficient shock wave of the desired energy level.

Another disadvantage with some lithotripter electrode assemblies is the inability to easily exchange one set of electrodes for another. For example, if the electrodes are to be reconditioned or refurbished, electrodes that are permanently attached cannot be removed and replaced.

Subsequent to the disclosure of fixed-gap electrode assemblies, adjustable gap assemblies were invented to overcome the difficulties associated with fixed-gap assemblies. One type, as disclosed by Patent EP 0.349.915 suffers from the disadvantage that it must be adjusted manually; another type, disclosed in U.S. Pat. No. 4,730,614 can only be adjusted in one direction.

Accordingly, there remains a need for an improved, self-adjusting lithotripter electrode assembly that allows a variety of energy levels to be employed, compensates for electrode bum-off, and increases the overall life of the electrode assembly.

SUMMARY OF THE INVENTION

The present invention relates to medical treatment using shock wave therapy and related method; more particularly, a self-adjusting lithotripter electrode assembly. The preferred embodiment of the electrode assembly includes an insulator assembly, an electrode arrangement, a charging system, a mechanism for measuring electrical voltages, a mechanism for adjusting the distance between inner and outer electrode tips, and a controller. The insulator assembly includes an insulator body having a hollow central portion with a threaded inner wall. The insulator assembly also includes inner and outer conductors that are electrically connected to the charging system and are physically connected to inner and outer electrodes, respectively. The electrodes are positioned such that their longitudinal axes are aligned and the tips of the electrodes are in relatively close physical proximity. The distance between the tips is defined as the spark gap. The charging system includes a capacitor and a voltage source. The electrical measuring mechanism includes a conventional meter device. The controller includes a microprocessor, microcomputer, or equivalent device.

The operation is as follows. A voltage is applied to the capacitor that is charged at a constant rate. When the voltage reaches a certain level, a spark is produced across the spark gap as the capacitor discharges. The electrical measuring device measures the actual discharge voltage and a corresponding signal is sent to the controller. The controller then compares the discharge voltage to an optimum, i.e., reference, discharge voltage. If the spark gap is correctly adjusted, the discharge of the second capacitor is at its maximum voltage and no correction is made. However, if the spark gap is too narrow, the discharge of the second capacitor occurs before the capacitor has achieved its maximum value. If the spark gap is too wide, there is either only a partial discharge after the capacitor has reached its maximum value or no discharge at all. In either case, the spark gap is not set to its optimum distance, resulting in an incomplete use of the energy stored in the capacitor. Accordingly, the controller issues a correction signal to initiate a spark gap adjustment, thus actuating the motor and associated components. The motor engages the gearbox that in turn moves the threaded element forward or rearward, thus positioning the inner conductor and the inner electrode such that the spark gap is of a distance capable of producing a spark at the optimum or reference voltage.

An alternate embodiment utilizes an additional capacitor and an inductor. The discharge of the first capacitor does not take place directly across the spark gap, but instead discharges to a second capacitor that is directly connected to the electrode conductors. When the voltage from the second capacitor reaches a sufficient value, a spark is then created across the spark gap. The controller compares the charge and discharge characteristics of the second capacitor. If a discrepancy exists between the actual discharge voltage and the reference discharge voltage, the controller computes the proper spark gap and issues a signal to the motor, which results in a spark gap adjustment as described above.

One advantage of the present invention includes a solution to the electrode burn-off problem by automatically maintaining a proper spark gap.

Another advantage of the present invention includes the ability to provide a wide spectrum of energy levels without the necessity of replacing the electrodes.

Still another advantage of the present invention includes the ability to easily replace the electrodes when needed.

Yet still another advantage of the present invention includes the elimination of manual adjustment of the spark gap.

Yet still another advantage of the present invention includes the ability to both widen and narrow the spark gap.

Additional advantages of the present invention will become apparent to those skilled in the art from the following detailed description of the preferred embodiment, which exemplifies the best mode of carrying out the invention.

The invention itself, together with further objects and advantages, can be better understood by reference to the following detailed description and the accompanying drawings.

DETAILED DESCRIPTION OF THE PRESENT INVENTION

Figure 1A:
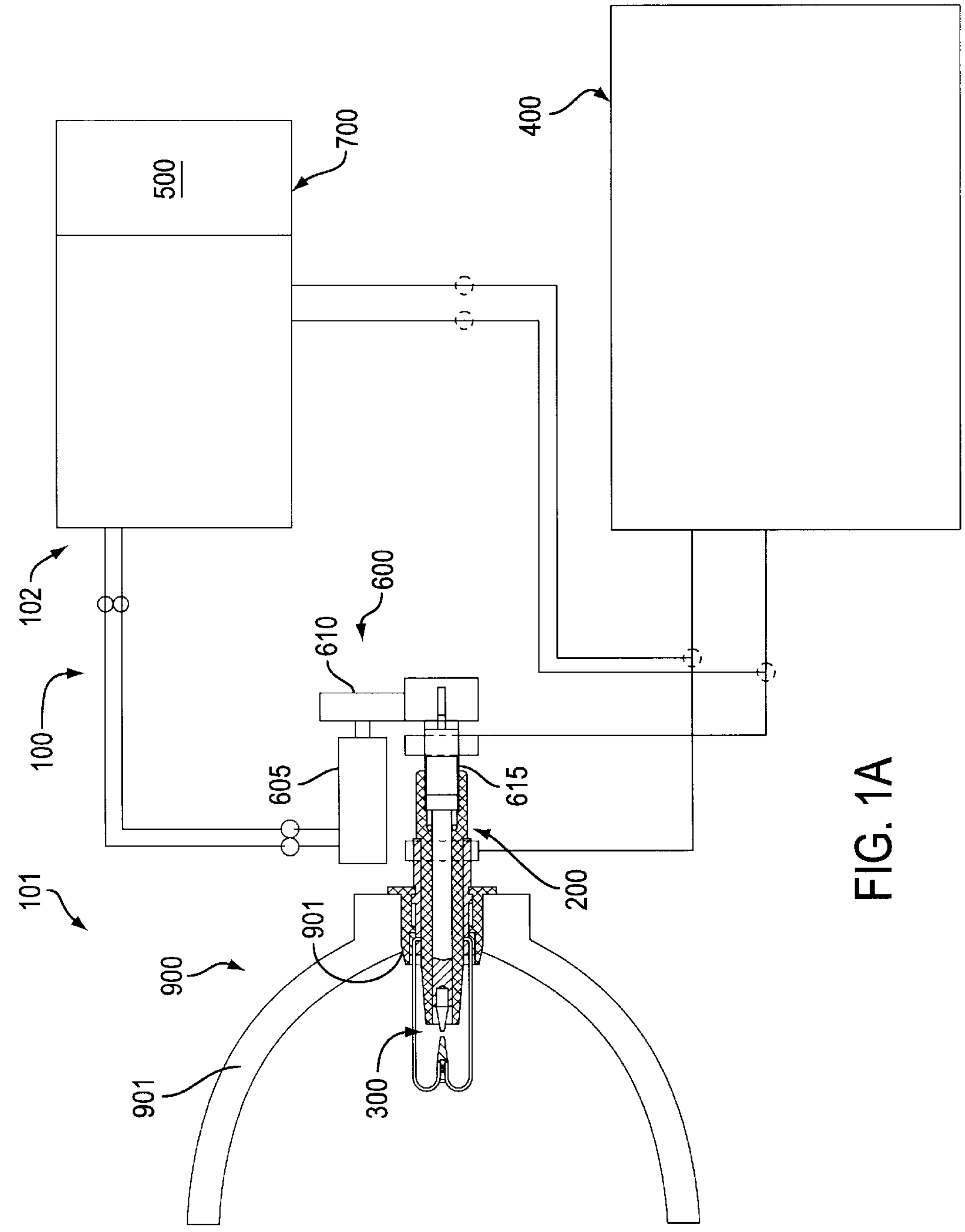
FIG. 1A is a system diagram of the preferred embodiment of the present invention.
Figure 1C:
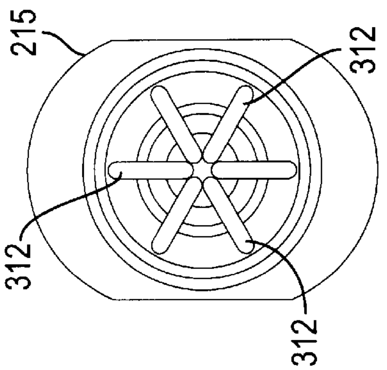
FIG. 1C is a forward end view of the electrode assembly shown in FIG. 1B.
Figure 1B:
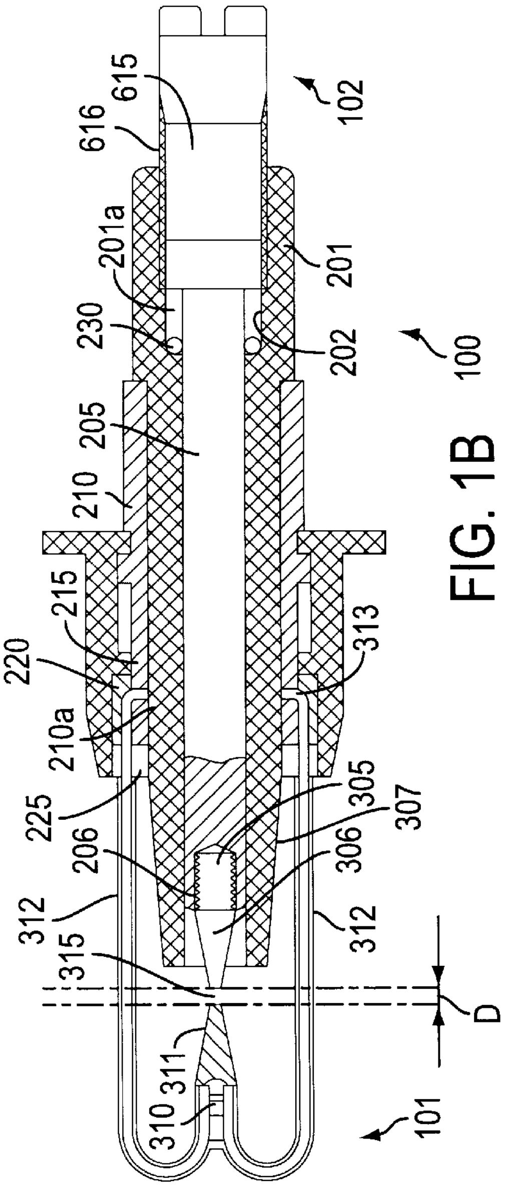
FIG. 1B is an enlarged side elevational view of the electrode assembly of the present invention.

Referring now to FIGS. 1A–1C, the preferred embodiment of the electrode assembly 100, which has a forward end 101 and a rearward end 102, includes a insulator assembly 200, an electrode arrangement 300, a charging system 400, a mechanism 500 for measuring electrical voltages, a mechanism 600 for adjusting the distance between inner and outer electrode tips, and a controller 700.

The insulator assembly 200 includes an insulator body 201 that is cylindrical in construction having a hollow central portion 201*a*. The insulator 201 has a threaded inner wall 202. The insulator 201 is mounted in a focusing device 900, the focus device 900 having an outer wall 901 with an opening 901*a* through which the insulator 201 is partially disposed. The insulator 201 also includes an outer locking ring 215, an inner locking ring 220, and a seal 225, best shown in FIG. 1B.

The insulator assembly 200 further includes an inner conductor 205 and an outer conductor 210. The inner conductor 205 is a rod-like component that is slidably positioned within the central portion 201*a* of the insulator body 201 as shown in FIG. 1B. In the preferred embodiment, the inner conductor 205 has a threaded forward end 206 for engaging an inner electrode 305, described in further detail below. The inner conductor 205 is made of an electrically conductive metal or equivalent material. The outer conductor 210 surrounds the insulator body 201 and is made of a material similar to or identical to that of the inner conductor.

The electrode arrangement 300 includes an inner electrode 305 and an outer electrode 310. The inner electrode 305 is a short, rod-like component and has a tapered tip 306 and a threaded rearward end 307. It is coaxially affixed to the inner conductor 205 via the threaded end 307 engaging the threaded end 206 of the inner conductor 205 as shown in FIG. 1B and is partially disposed within the insulator 201. Alternately, the inner electrode 305 may be soldered to the inner conductor 205 or attached in a similar manner. The inner electrode 305 is made of an electrically conductive metal or equivalent material and is electrically connected to the inner conductor 205.

The outer electrode 310 is a short, rod-like component and also has a tapered tip 311. The outer electrode 310 is supported by the outer electrode cage members 312, each of which includes a hook 313 that is formed at a generally right angle to the cage member 312. The outer electrode cage members 312 are J-shaped at the forward end, best shown in FIG. 1B, to help alleviate the stress caused by the high voltage. The outer electrode 310 is mounted to the insulator 201 at the forward end 101 of the electrode assembly 100 as shown. The outer electrode 310 is usually attached to the outer electrode cage 312 by a soldering process or equivalent. The outer electrode 310 is positioned such that the longitudinal axes of the inner and outer electrodes 305 and 310 are aligned and the tips 306 and 311 of the electrodes 305 and 310 are in relatively close physical proximity. The distance D between the tip 306 of the inner electrode 305 and the tip 311 of the outer electrode 310 is defined as the spark gap 315.

The charging system 400 includes a high voltage switch 401, typically a thyratron in the preferred embodiment, and a capacitor 405 that is a high-voltage variety of standard construction. It is electrically connected to the inner and outer conductors 205 and 210. The capacitor 405 is also electrically connected to a voltage source (not shown) and the controller 700 as shown in FIG. 1A.

The device 500 for measuring electrical voltages is a conventional electrical meter (not shown) or equivalent. It may be an integral part of the controller 700, described below, or may be a separate unit.

The mechanism 600 for adjusting the spark gap 315 includes a motor 605, a gearbox 610, and a threaded element 615 having threads 616. The motor 605 is mechanically connected to the gearbox 610 that in turn is mechanically connected to the threaded element 615. The threaded element 615 is partially disposed within the rearward end of the insulator 201 such that the threads 616 on the outer surface of the threaded element 615 engage the threaded inner wall 202 of the insulator 201 at the rearward end 102 of the electrode assembly 100. Alternately, the inner conductor 205 and the threaded element 615 may be a formed as a single integral component.

The controller 700 typically includes a microprocessor, microcomputer, or other like device (not shown) capable of performing at least complex mathematical and comparative functions. The controller 700 is electrically connected to the motor 605 and the capacitor 405 and 410.

One feature of the present invention includes the ability to quickly change electrodes for reconditioning or other maintenance. First, the outer locking ring 215 is moved in the rearward direction. The inner locking ring 220 is also moved in the same direction, thus allowing the outer electrode cage hooks 313 to disengage from the groove 210*a* in the insulator body 210. The outer electrode 310 and cage 312 is then pulled away from the electrode assembly 100. With the outer electrode 310 and cage 312 out of the way, the inner electrode 305 may be unscrewed from the inner conductor 205. New electrodes may then be easily installed with the hooks 313 of the new cage 312 engaging the groove 210 and locking rings 215 and 220 and spacer 225 frictionally retaining the hooks 313 in place.

The operation of the electrode assembly 100 of the present invention is as follows. A voltage V is applied to the capacitor 405, which is charged at a constant rate. When the voltage reaches a certain level $V_d$, a spark is produced across the spark gap 315 as the capacitor 405 discharges. The actual discharge voltage $V_d$ is measured by the electrical measuring device 500 and a corresponding signal is sent to the controller 700. The controller 700 then compares the discharge voltage $V_d$ to an optimum, i.e., reference, discharge voltage $V_{dref}$. If a discrepancy exists between the actual discharge voltage $V_d$ and the reference discharge voltage $V_{dref}$, the controller 700 computes the proper spark gap 315 and issues a signal to the motor 605. The motor 605 engages the gearbox 610 that in turn moves the threaded element 615 forward or rearward, thus positioning the inner conductor 205 and the inner electrode 305 such that the spark gap 315 is of distance capable of producing a spark at the optimum or reference voltage $V_{dref}$.

Figure 2:
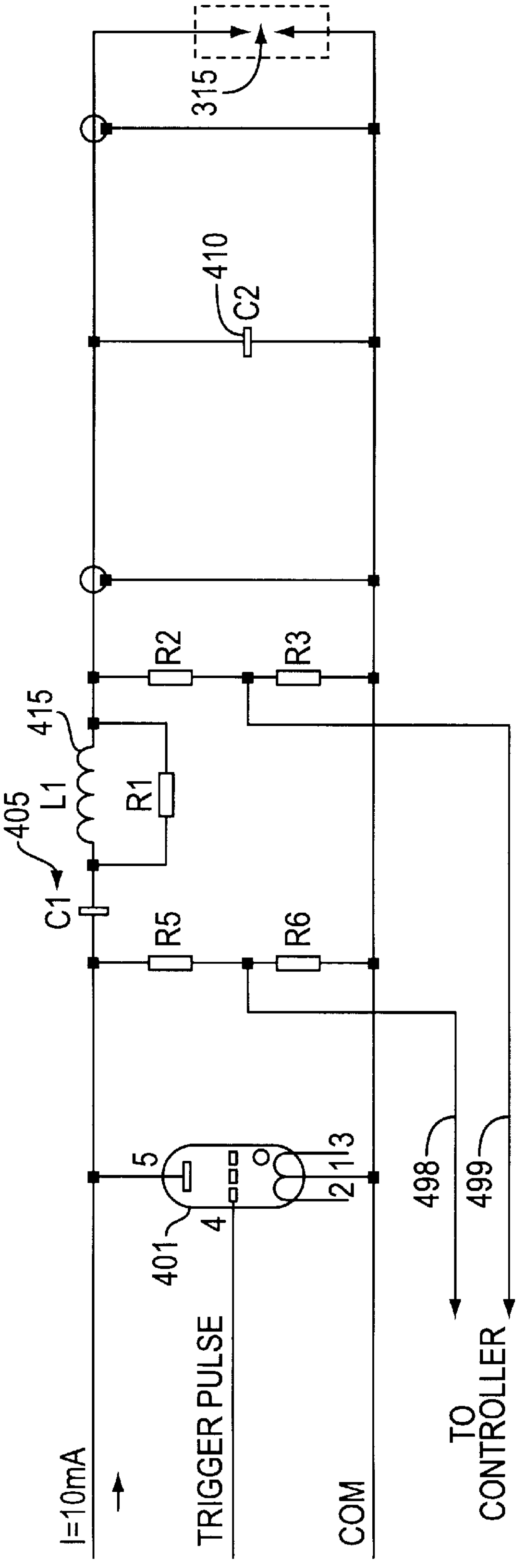
FIG. 2 is an electrical schematic of an alternate embodiment of the present invention.

In an alternate embodiment of the present invention, a second capacitor 410 is used that is electrically connected in series with the first capacitor 405 with an inductor 415 in between the two capacitors 405 and 410 as shown in the electrical schematic FIG. 2. The high voltage switch 401 used is a thyratron or equivalent. The controller 700 is also connected to the second capacitor 410.

Figures 3A, 3B:
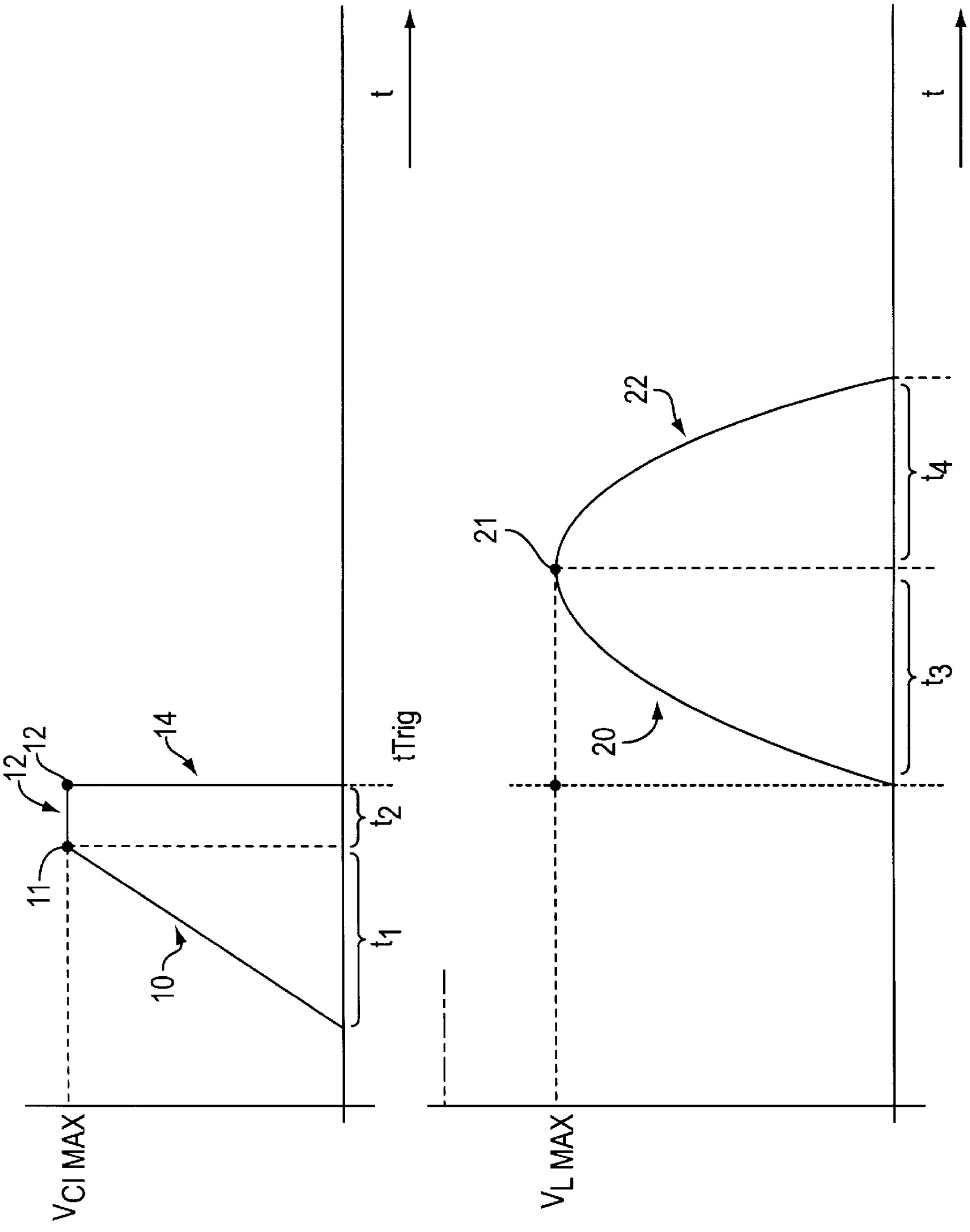
FIG. 3A is a graph of the voltage experienced over time of the first capacitor of the alternate embodiment shown in FIG. 2.
FIG. 3B is a graph of the voltage experienced over time of the inductor of the alternate embodiment shown in FIG. 2.
Figure 3C:
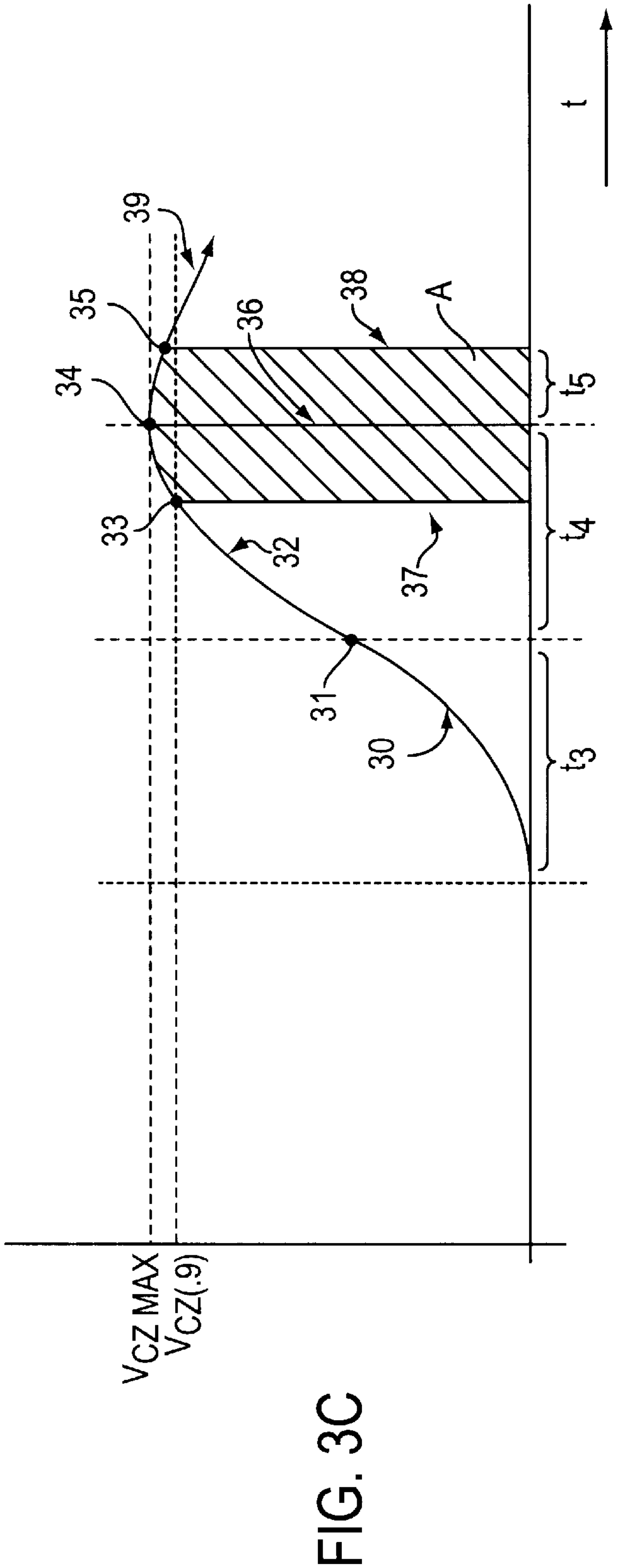
FIG. 3C is a graph of the voltage experienced over time of the second capacitor of the alternate embodiment shown in FIG. 2.

FIGS. 3A–3C are voltage vs. time graphs that depict the operation, that is, the sequence of electrical events, during the formation of a spark in the alternate embodiment. A voltage V is applied to the capacitor 405 that is charged at a linear rate over time $t_1$, depicted by curve portion 10. The controller 700, via line 498 as shown in FIG. 2, monitors the charging of the capacitor 405. The maximum load of the capacitor 405 is reached at point 11 and remains constant, i.e., fully charged over time $t_2$, depicted by curve portion 12. At a time certain, point 11, the switch 401 is actuated and a controlled discharge is initiated, depicted by curve portion 14.

As the voltage from the first capacitor 405 is discharged, the voltage experienced by L1 begins to increase, as depicted by curve portion 20 in FIG. 3B and the second capacitor 410 begins to charge, depicted by curve portion 30 in FIG. 3C, both occurring over time period $t_3$. At the end of time period $t_3$, the voltage experienced by $L_1$ reaches its maximum, $V_{C1max}$, shown as point 21 in FIG. 3B and the curve portion 30 in FIG. 3C reaches a point of inflection 31, i.e., the point where the slope of the curve 30 changes from positive to negative.

During time period $t_4$, the voltage experienced by the inductor 415 drops off as shown by curve portion 22 in FIG. 3B; the capacitor 410 continues to charge as shown by curve portion 32, although the rate of charge is decreasing. As the voltage experienced by the inductor 415 reaches zero at the end of time period $t_4$, the voltage $V_{C2max}$ of the second capacitor 410 reaches its maximum value as depicted by point 34 in FIG. 3C and the second capacitor 410 is fully charged. It is at this point, ideally, that the second capacitor 410 should discharge and a spark should form, as depicted by curve portion 36. A spark formed at this point in time indicates that the spark gap 315 is at its optimum distance D and that all the energy in the second capacitor 410 is being used to form the spark. A spark that is produced before point 34 in FIG. 3C is reached indicates that the spark gap 315 is too narrow; a spark that is produced after point 34 is reached indicates the spark gap 315 is too wide. Generally speaking, a spark that is produced at between 90% and 100% of the second capacitor's maximum voltage $V_{C2max}$ is considered acceptable. In other words, a spark produced in the hatched region A between curve portions 37 and 38 is considered acceptable for the present invention, although acceptable error parameters can be varied. The controller 700, via line 499 as shown in FIG. 2, monitors the charging and discharging of the capacitor 410.

If the spark gap 315 is much narrower than optimum, then a spark will be formed prior to the voltage curve reaching 90% of the maximum, $V_{C2(.9)}$ value, shown by point 33 in FIG. 3C. In such a case, the controller 700 issues a correction signal to the motor 605 and the spark gap 315 would be adjusted (made wider) by the method described above. If, on the other hand, the spark gap 315 is much wider than optimum, then either a) a spark will be formed subsequent to the voltage curve dropping off 90% of the maximum, $V_{C2(.9)}$ value, shown by point 35 in FIG. 3C, or b) no spark will be produced at all, as shown by curve portion 39 in FIG. 3C. In such a case where the spark gap 315 is much too wide, the controller 700 issues a correction signal to the motor 605 and the spark gap 315 would be physically adjusted (made narrower) by the method described above.

To increase the accuracy of the correction process described above, it is possible to examine a series of charges and discharges before making a spark gap correction, as opposed to examining only one charge and discharge cycle prior to making a correction. The controller 700 is programmed to analyze a predetermined number of charges and discharges prior to making a determination. The series is then statistically analyzed and only then is a correction made, if necessary. Thus, a single false voltage measurement or other glitch would not result in an unnecessary correction that would ultimately have to be recorrected.

Figure 4A:
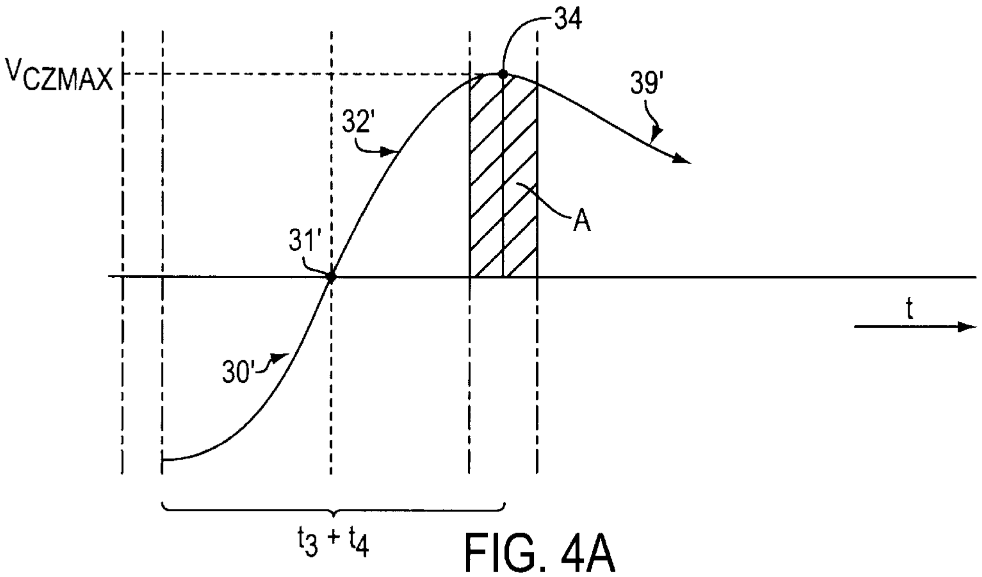
FIG. 4A is a graph of the voltage experienced over time of the second capacitor of the alternate embodiment shown in FIG. 2, including a voltage offset.
Figure 4B:
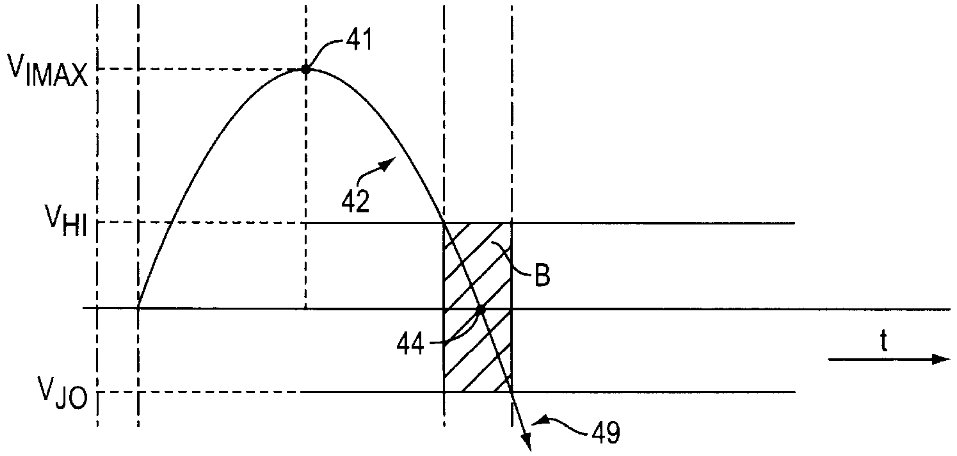
FIG. 4B is a graph of the integral of the voltage experienced over time of the second capacitor of the alternate embodiment shown in FIG. 2.

As discussed above, it is possible to determine the optimum spark gap 315 by examining the charge and discharge voltage characteristics of the second capacitor. However, an even more accurate method is available. The method is accomplished by adding a negative 50% of the reference voltage to the curve of the second capacitor 410 as shown in FIG. 4A, resulting in a new curve 30'/32' that has a point of inflection 31' intersecting with the time axis. The new charge/discharge curve is then integrated and inverted by the controller 700, resulting in an integral curve shown in FIG. 4B. The maximum integrated value, $V_{imax}$, shown as point 41 in FIG. 4B, corresponds to the point of inflection 31' in FIG. 4A. If the discharge of the second capacitor 410 occurs in the acceptable range shown by hatched area A in FIG. 4A, such as is the depicted by point 34', the discharge will appear in the acceptable range depicted by hatched area B in FIG. 4B as point 44. A discharge that occurs too soon (which would appear along curve portion 32' in FIG. 4A) because of a spark gap that is too narrow appears on the integral curve portion 42 above the upper reference value $V_{ihi}$. Similarly, a discharge that occurs too late, or not at all (which would appear along curve portion 39' in FIG. 4A), because of a spark gap that is too wide will appear on the integral curve portion 49 below the lower reference value $V_{ilo}$. In either case, the unacceptable discharge value would result in a correction signal being sent by the controller 700. The most important benefit of integrating the voltage characteristic curve of the second capacitor 410 is a "magnified" look at the acceptable range resulting in a more accurate account of events.

The integration technique can be combined with the statistical analysis approach, both described above, to obtain an extraordinarily accurate method of determining and adjusting the spark gap 315.

Of course, it should be understood that a wide range of changes and modifications could be made to the exemplary embodiments described above. It is therefore intended that the foregoing detailed description be regarded as illustrative rather than limiting and that it be understood that it is the following claims, including all equivalents, which are intended to define the scope of this invention.

What is claimed is:

1. An electrode assembly, comprising:

an insulator having a generally cylindrical body and a hollow interior having a threaded inner surface;

an inner conductor disposed within said hollow interior and an outer conductor attached to the outer surface of said insulator;

an inner electrode being connected to said inner conductor, an outer electrode cage being connected to said outer conductor, an outer electrode being connected to said outer electrode cage, said inner and outer electrodes being opposed and coaxially aligned, said electrodes having tips, the distance between said tips defining a spark gap;

a first capacitor being connected to said inner and said outer conductors;

an electrical meter connected to said capacitor;

a device for adjusting the spark gap comprising a motor, a gearbox connected to said motor, and a threaded positioning element being engaged with said threaded inner surface of said insulator, said positioning element further being connected to said inner conductor; and, a controller being electrically connected to said motor, said capacitor, and said electrical meter, said controller comparing the discharge voltage of said capacitor to a predetermined reference value and issuing a correction signal to said motor when said discharge voltage differs from said predetermined reference value, whereby moving said tip of said inner electrode closer to or farther away from said tip of said outer electrode.

2. The electrode assembly of claim 1 further comprising:

a second capacitor electrically connected to said first capacitor and said meter; said second capacitor being connected to said inner and outer conductors;

an inductor electrically connected to said first and said second capacitors;

whereby said controller compares the charge and discharge voltages of said second capacitor to predetermined reference values and issues a correction signal to said motor when said charge and discharges voltage differ from said predetermined reference values, whereby moving said tip of said inner electrode closer to or farther away from said tip of said outer electrode.

3. The electrode assembly according to claim 1 further comprising:

a groove formed in the outer surface of said insulator capable of receiving said outer electrode cage;

an inner locking ring slidably engaged with said electrode body, said inner locking ring for retaining said outer electrode cage within said groove;

an outer locking ring slidably engaged with said electrode body and with said inner locking ring, said outer locking ring for retaining said inner locking ring.

4. The electrode assembly according to claim 3 wherein said inner conductor further comprises a threaded end and said inner electrode further comprises a threaded end, said threaded end of said inner electrode being engaged with said threaded end of said inner conductor.

5. A lithotripter electrode assembly, comprising:

a insulator assembly comprising an insulator body, an inner conductor and an outer conductor;

an electrode arrangement comprising an inner electrode having a tip and an outer electrode having a tip, said inner and outer electrodes being coaxially aligned and said tips being in relatively close physical proximity wherein the distance between said tips define a spark gap, said inner electrode being electrically connected to said inner conductor and said outer electrode being connected to said outer conductor;

a charging system comprising at least one capacitor and a voltage source, said voltage source being electrically connected to said capacitor and said capacitor being electrically connected to said inner and outer conductors;

means for measuring a discharge voltage of said capacitor, said measuring means electrically connected to said charging system; and, means for adjusting said spark gap, said adjusting means being connected to said electrode arrangement and further being electrically connected to said measuring means, said adjusting means being responsive to a discharge voltage of said capacitor.

6. The lithotripter electrode assembly according to claim 5 wherein said measuring means comprises a voltage meter.

7. The lithotripter electrode assembly according to claim 5 wherein said measuring means comprises an oscilloscope.

8. The lithotripter electrode assembly according to claim 5 wherein said adjusting means comprises:

a motor;

a gearbox connected to said motor; and, a positioning element being connected to said gearbox and said inner conductor.

9. The lithotripter electrode assembly according to claim 8 wherein said adjusting means further comprises:

a controller being electrically connected to said motor, said capacitor, and said measuring means, said controller comparing the discharge voltage of said capacitor to a predetermined reference value and issuing a correction signal to said motor when said discharge voltage differs from said predetermined reference value, whereby moving said tip of said inner electrode closer to or farther away from said tip of said outer electrode.

10. The lithotripter electrode assembly according to claim 8 wherein said controller comprises a microprocessor.

11. A method of adjusting a spark gap of a lithotripter electrode assembly comprising the steps of:

applying a voltage to a first capacitor being electrically connected to a first conductor and a second conductor whereby creating a spark across said spark gap;

measuring the actual discharge curve of said spark created across said spark gap;

comparing said actual discharge curve with a predetermined reference curve; and, adjusting said spark gap based on a difference between said actual discharge curve and said reference discharge curve.

12. The method according to claim 11 further comprising the steps of:

applying the output voltage of said first capacitor to a second capacitor;

measuring the actual charge curve of said second capacitor;

comparing said actual charge curve of said second capacitor with a reference charge curve;

adjusting said spark gap based on a difference between said actual charge and discharge curves and said reference charge and discharge curves.

13. The method according to claim 12 wherein said steps of comparing comprising said actual charge and discharge curves with said reference charge and discharge curves comprise:

integrating said charge and discharge curve; and, inverting said charge and discharge curve;

whereby determining whether said spark gap is adjusted properly by determining whether said discharge of said second capacitor occurs within an acceptable range.

14. The method according to claim 13 further comprising the step of offsetting the actual charge and discharge curve by a −50% of the reference voltage.

15. The method according to claim 12 wherein said step of adjusting said spark gap comprises:

issuing a correction signal from a controller to widen or narrow said spark gap.

16. A method of adjusting a spark gap of a lithotripter electrode comprising the steps of:

charging a first capacitor;

discharging said first capacitor into a second capacitor whereby charging said second capacitor until said second capacitor discharges across said spark gap;

measuring the actual charging and discharging voltages of said second capacitor;

comparing said actual charging and discharging voltages of said second capacitor with reference charging and discharging voltages; and, adjusting said spark gap based on a difference between said actual charging and discharging voltages of said second capacitor and said reference charging and discharging voltages such that a subsequent discharge of said second capacitor occurs at the maximum load of said second capacitor.

17. The method according to claim 16 wherein said steps of comparing said actual charge and discharge voltages with said reference charge and discharge voltages comprise:

integrating said charge and discharge voltages; and, inverting said charge and discharge voltages;

whereby determining whether said spark gap is adjusted properly by determining whether said discharge of said second capacitor occurs within an acceptable range.

18. The method according to claim 17 further comprising the step of offsetting the actual charge and discharge voltages by a −50% of the reference voltage.

19. A method of adjusting a spark gap of a lithotripter electrode comprising the steps of:

creating a spark across said spark gap by charging a capacitor until said capacitor discharges across said spark gap;

measuring the actual discharging voltage of said capacitor;

comparing said actual discharging voltage of said capacitor with a reference discharging voltage; and, adjusting said spark gap based on a difference between said actual discharging voltages of said capacitor and said reference discharging voltages.

20. The method according to claim 19 further comprising the steps of:

discharging said capacitor to a second capacitor to create a spark across said spark gap; and, adjusting said spark gap based on a difference between said actual charging and discharging voltages of said second capacitor and said reference charging and discharging voltages.

21. The method according to claim 20 further comprising the steps of:

recording a succession of charges and discharge voltage values; and, statistically analyzing said succession of values to determine a representative voltage value; and comparing said representative voltage value with a reference voltage value; and, adjusting said spark gap based on a difference between said representative voltage value with a reference voltage value.

22. The method according to claim 21 wherein said steps of comparing the representative voltage value with a reference voltage value comprises:

integrating said representative voltage values; and, inverting said representative voltage values;

whereby determining whether said spark gap is adjusted properly by determining whether said discharge of said second capacitor occurs within an acceptable range.

23. The method according to claim 22 further comprising the step of offsetting the actual representative voltage values by a −50% of the reference voltage.

24. A lithotripter electrode assembly, comprising:

a insulator assembly comprising an insulator body and a pair of conductors;

an electrode arrangement comprising a pair of electrodes wherein the distance between said each of pair of electrodes defines a spark gap, said pair of electrodes being electrically connected to said pair of conductors;

a charging system comprising at least one capacitor and a voltage source, said voltage source being electrically connected to said capacitor and said capacitor being electrically connected to said pair of conductors;

means for measuring a discharge voltage of said capacitor, said measuring means electrically connected to said charging system; and, means for adjusting said spark gap, said adjusting means being connected to said pair of electrodes and further being electrically connected to said measuring means, said adjusting means being responsive to a discharge voltage of said capacitor.

25. The electrode assembly according to claim 24 further comprising a second capacitor wherein said adjusting means is responsive to charge and discharge voltages of said second capacitor.

* * * * *

UNITED STATES PATENT AND TRADEMARK OFFICE

CERTIFICATE OF CORRECTION

PATENT NO. : 6,217,531 B1
DATED : April 17, 2001
INVENTOR(S) : Ralph Reitmajer

It is certified that error appears in the above-identified patent and that said Letters Patent is hereby corrected as shown below:

Title page,
Item [73], Assignee section, change "ITS" to -- MTS --.

Signed and Sealed this

Twenty-third Day of October, 2001

*Attest:*

Nicholas P. Godici

NICHOLAS P. GODICI

*Attesting Officer*

*Acting Director of the United States Patent and Trademark Office*